US008690773B2

(12) United States Patent
Bagan

(10) Patent No.: US 8,690,773 B2
(45) Date of Patent: Apr. 8, 2014

(54) SECURITY ENABLED MEDICAL SCREENING DEVICE

(76) Inventor: Kenneth J. Bagan, Highland Park, IL (US)

( * ) Notice: Subject to any disclaimer, the term of this patent is extended or adjusted under 35 U.S.C. 154(b) by 0 days.

(21) Appl. No.: 13/114,880

(22) Filed: May 24, 2011

(65) Prior Publication Data

US 2012/0010897 A1 Jan. 12, 2012

Related U.S. Application Data

(63) Continuation of application No. 11/560,322, filed on Nov. 15, 2006, now Pat. No. 7,988,628, which is a continuation-in-part of application No. 11/550,663, filed on Oct. 18, 2006, now Pat. No. 7,988,627.

(51) Int. Cl.
*A61B 5/00* (2006.01)
*G06F 19/00* (2011.01)

(52) U.S. Cl.
CPC .................................. *G06F 19/3418* (2013.01)
USPC .......................................................... 600/301

(58) Field of Classification Search
USPC .................................. 600/300–301; 705/2–5
See application file for complete search history.

(56) References Cited

U.S. PATENT DOCUMENTS

| | | | |
|---|---|---|---|
| 6,403,897 B1 | 6/2002 | Bluth et al. | |
| 6,478,736 B1 | 11/2002 | Mault | |
| 6,579,231 B1 | 6/2003 | Phipps | |
| 6,595,929 B2 | 7/2003 | Stivoric et al. | |
| 6,689,057 B1 * | 2/2004 | Shinsel et al. | 600/300 |
| 6,692,436 B1 | 2/2004 | Bluth et al. | |
| 6,898,299 B1 | 5/2005 | Brooks | |
| 7,736,272 B2 * | 6/2010 | Martens | 482/8 |
| 8,027,822 B2 * | 9/2011 | Turgiss et al. | 703/11 |
| 2004/0034289 A1 * | 2/2004 | Teller et al. | 600/300 |
| 2004/0044560 A1 * | 3/2004 | Giglio et al. | 705/10 |
| 2004/0117214 A1 * | 6/2004 | Shea | 705/2 |
| 2004/0260577 A1 | 12/2004 | Dahlin et al. | |
| 2005/0192841 A1 | 9/2005 | Hays et al. | |
| 2005/0245793 A1 * | 11/2005 | Hilton et al. | 600/300 |
| 2006/0058155 A1 * | 3/2006 | Kumar | 482/4 |
| 2006/0089840 A1 * | 4/2006 | May | 705/1 |
| 2006/0106646 A1 * | 5/2006 | Squilla et al. | 705/3 |
| 2006/0106734 A1 * | 5/2006 | Hoffman et al. | 705/64 |
| 2006/0217232 A1 * | 9/2006 | Kondrat et al. | 482/3 |

(Continued)

OTHER PUBLICATIONS

International Search Report from PCT/US2007/81804 filed Oct. 18, 2007.

*Primary Examiner* — Bill Thomson
*Assistant Examiner* — Bobby Soriano
(74) *Attorney, Agent, or Firm* — Miller, Matthias & Hull LLP

(57) ABSTRACT

Embodiments of the invention pertain to networked kiosks capable of providing enhanced health and/or entertainment and/or advertising information. In an embodiment of the invention, biometric measurement devices coupled with a communications infrastructure implement a system of secure information exchange and enhanced user security. In an embodiment of the invention, a user's cell phone wirelessly connected via the machine to a call center or other responder to allow for consultation when appropriate. In an embodiment of the invention, a security/verification system is built into the kiosk, so as to be able to verify a user's identity. For example, one or more cameras associated with the kiosk provide various types of visual data usable for security purposes e.g., retinal scan data, face recognition parameter data, and so on. In further embodiments of the invention, other security features are provided additionally or alternatively.

18 Claims, 6 Drawing Sheets

(56) References Cited

U.S. PATENT DOCUMENTS

| | | |
|---|---|---|
| 2007/0011027 A1* | 1/2007 | Melendez ......................... 705/2 |
| 2007/0033068 A1* | 2/2007 | Rao et al. ......................... 705/2 |
| 2007/0033069 A1* | 2/2007 | Rao et al. ......................... 705/2 |
| 2007/0136093 A1* | 6/2007 | Rankin et al. .................... 705/2 |
| 2007/0150310 A1* | 6/2007 | Wiegand et al. ................. 705/2 |

* cited by examiner

SECURITY ENABLED MEDICAL SCREENING DEVICE

RELATED APPLICATIONS

This application is a continuation of U.S. Ser. No. 11/560,322, filed Nov. 15, 2006, entitled Security Enabled Medical Screening Device, which is a continuation-in-part of U.S. patent application Ser. No. 11/550,663, filed on Oct. 18, 2006, entitled Medical Screening And Advertising Process And Arrangement, which is herein incorporated by reference in its entirety for all that it teaches without exclusion of any part thereof.

BACKGROUND OF THE INVENTION

A number of companies have successfully provided public kiosk blood pressure machines for a number of years. These devices allow users to obtain a reading of their blood pressure during a break while shopping etc. Users are concerned about their blood pressure primarily for health reasons, and are typically unable to otherwise obtain a reading without visiting a doctor or other health practitioner. The blood pressure machines are thus very popular and millions of people have availed themselves of the services provided by such machines. Blood pressure kiosks can be used for advertising purposes to generate an additional revenue stream such as by having large consumer product companies advertise. However, such known systems are less than ideal for a number of reasons that will become apparent hereinafter.

The present inventor has been instrumental in the biometrics area for almost 30 years. In that time, he has created new and useful systems and advanced the state of the art. In one example he has created a system of blood pressure kiosks in university settings by deploying a number of LifeClinic® model 9000 units to colleges free of charge. Although the number of units deployed at that time was small, the exercise did show that the machines were potentially popular with university students and staff. However, that implementation did not employ or benefit from the structures, methods, and techniques that are described herein for improving the state of the art.

OBJECTS AND SUMMARY OF THE INVENTION

Certain embodiments of the invention pertain to biometric measurement devices coupled with a communications infrastructure to implement a system of secure information exchange and enhanced user security. In an embodiment of the invention, a global network of kiosks provides the described services and functionality. Although the examples herein pertain primarily to the biometric parameters of weight, blood pressure, pulse rate, body fat and blood oxygen (via oximeter), it will be appreciated by those of skill in the art that any suitable biometric measurement device may be used additionally or alternatively.

In an embodiment of the invention, a LifeClinic® model LC500 unit is used to implement the health kiosk, but any machine with similar functionality may be used instead. The tests that are currently available on this machine are weight, blood pressure, pulse rate, body fat and blood oxygen. In addition, diabetics can download a history of readings from certain glucose meters into an internet-connected kiosk. At a later time, the user can retrieve the readings on a public (i.e., LifeClinic®) website and/or dedicated website. In addition, users of the interne-connected machines may email their history of readings to their doctors in preparation for an upcoming physical exam etc.

In an embodiment of the invention, a kiosk user's cell phone is used to wirelessly connect, via the machine to a call center, doctor, or emergency center. This allows for an emergency consultation when appropriate and also alleviates concerns regarding the sanitation of a dedicated phone attached to the kiosk. Thus, the user can talk to the device sponsor's call center, e.g., a twenty-four hour call center or service location or any other suitable location for any information he or she needs using their own cell phone. This service addresses a major unsolved shortcoming of prior unattended systems, i.e., the inability to provide counseling or consulting related to abnormal readings that make a consultation advisable and/or desirable.

Very high readings cause the kiosk to connect the user's cell phone to the kiosk (e.g., via Bluetooth) and then through to a call center representative for counseling. When communicating with the user's cell phone, the kiosk may target devices within a small enough radius to likely include the cell phone, e.g., 2 or 3 feet.

In an embodiment of the invention, a security/verification system is built into the kiosk. In particular, it is important for kiosk sponsors who provide incentives linked to user health to be able to verify that the user is indeed the person that they represent themselves to be. Moreover, patient health information is sensitive and protected information, and indeed, the 2006 National Patient Safety Goals for Behavioral Health Care" suggest that two unique patient identifiers be obtained prior to providing health services or confidential health information.

One area where significant incentives may be provided and hence where security will be important is the area of insurance incentives. In particular, the inventor anticipates that insurers will enroll with a kiosk system host to receive user medical information from such kiosks and to provide targeted advertising and incentives through the kiosks. In particular, a user may use any one of the global network of kiosks to take a measurement of interest, e.g., weight, body fat percentage, or blood pressure, and this information will be transmitted to the enrolled insurer. If the user's current and prior measurements show a positive trend (e.g., losing body fat) at an acceptable rate (e.g., 2 pounds per week) or in an acceptable amount (e.g., 10 pounds), then the insurer will provide a reward to the user. Rewards may be rebates, gift cards, reduced insurance rates, and so on.

In an embodiment of the invention, the kiosk, whether providing health-related measurements or not, displays information of general interest to the user. For example, the kiosk may display a stock ticker or 5-day weather forecast.

In an embodiment of the invention, a camera is built into the kiosk pod so that the call center representative can see the customer during a conversation. The camera provides the additional benefit of allowing visual data gathering. Types of visual data usable for security purposes include retinal scan data, face recognition parameter data, and so on. In further embodiments of the invention, other security features are provided additionally or alternatively. For example, a fingerprint scanner may be used in conjunction with face recognition or retinal scan identification to verify a user's identity. In addition, the camera may be used to verify that the user is within a predetermined distance of the camera, indicating a high likelihood that the user is seated at the machine. Moreover, the camera may also be used to store a photograph of the user for later verification to discourage cheating by "standing in." In other words, the knowledge that a picture has been stored will discourage unscrupulous users from having their friends "stand in" for them to manipulate the test results. Other features according to various embodiments of the invention will be discussed in the examples below.

DETAILED DESCRIPTION OF THE INVENTION

As discussed above, certain embodiments of the invention pertain to biometric measurement devices coupled to a wide area network such as the Internet or other communications infrastructure and/or network. The link to the network may be implemented by way of wired or wireless connections or a combination thereof, and while high speed connections such as DSL are preferred, slower connections may instead be used. The physical structure and features of a biometric kiosk usable within embodiments of the invention was described in detail in the related application referenced above, and that description is incorporated by reference and will thus not be repeated at length herein.

Figure 1:
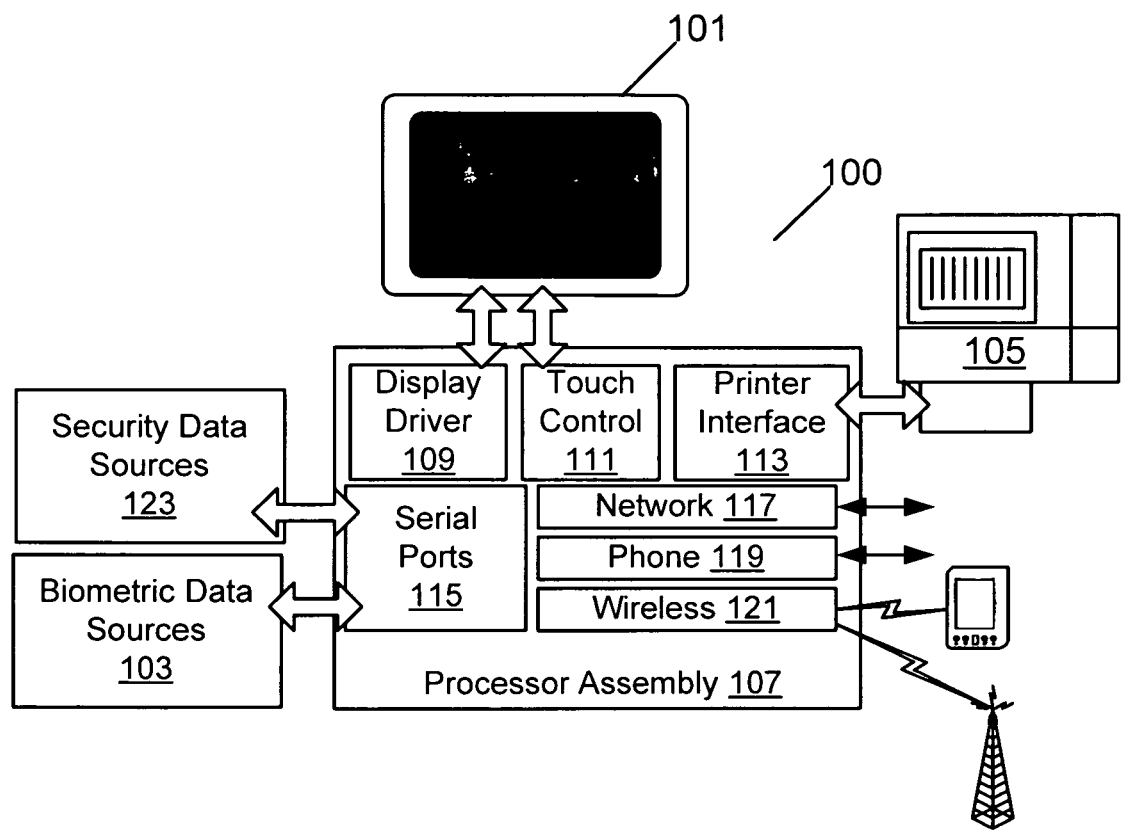
FIG. 1 is a schematic diagram of a kiosk usable within embodiments of the invention.

FIG. 1 is a schematic diagram of a kiosk usable within embodiments of the invention. The kiosk 100 comprises biometric data sources 103 (e.g., blood pressure cuff and associated electronics, scale and associated electronics, etc.), a display 101 and a printer 105.

These elements 101, 103, 105 are linked, typically by wired connections, to a processor assembly 107. The display 101 interfaces with the processor assembly 107 via a display driver 109 and a touch control module 111. The touch control module 111 receives and processes touch screen inputs from the display 101. The biometric data sources 103 interfaces with the processor assembly 107 via serial ports 115. Finally, the printer 105 interfaces with the processor assembly 107 via a printer interface 113.

The processor assembly 107 also comprises data links to external data sinks/sources. For example, in the illustrated embodiment of the invention, the processor assembly 107 comprises a network communication module 117, a phone communication module 119, and a wireless communication module 121. As will be discussed in greater detail below, the wireless communication module 121 allows connectivity to a cellular network and/or to local wireless devices (e.g., a PDA or cell phone) via a short range protocol such as Bluetooth. The network communication module 117 provides connectivity (wired or wireless) to one or more networks such as a local area network (LAN) and the Internet.

In addition to the features and elements noted above, the kiosk 100 further comprises a plurality of security data sources 123 linked to kiosk 100 via the serial ports 115 or otherwise as appropriate. The security data sources 123 comprise equipment usable to gather user-identifiable information for purposes of user verification. This is important both to protect sponsors from fraud as well as to protect users from unauthorized access to their biometric or other data. The security data, sources 123 may include one or more cameras for retinal scanning, face recognition, and visual record-keeping purposes (e.g., for potential verification of past test results), as well as a fingerprint scanner for additional security and cross-checking for validation.

Figure 2:
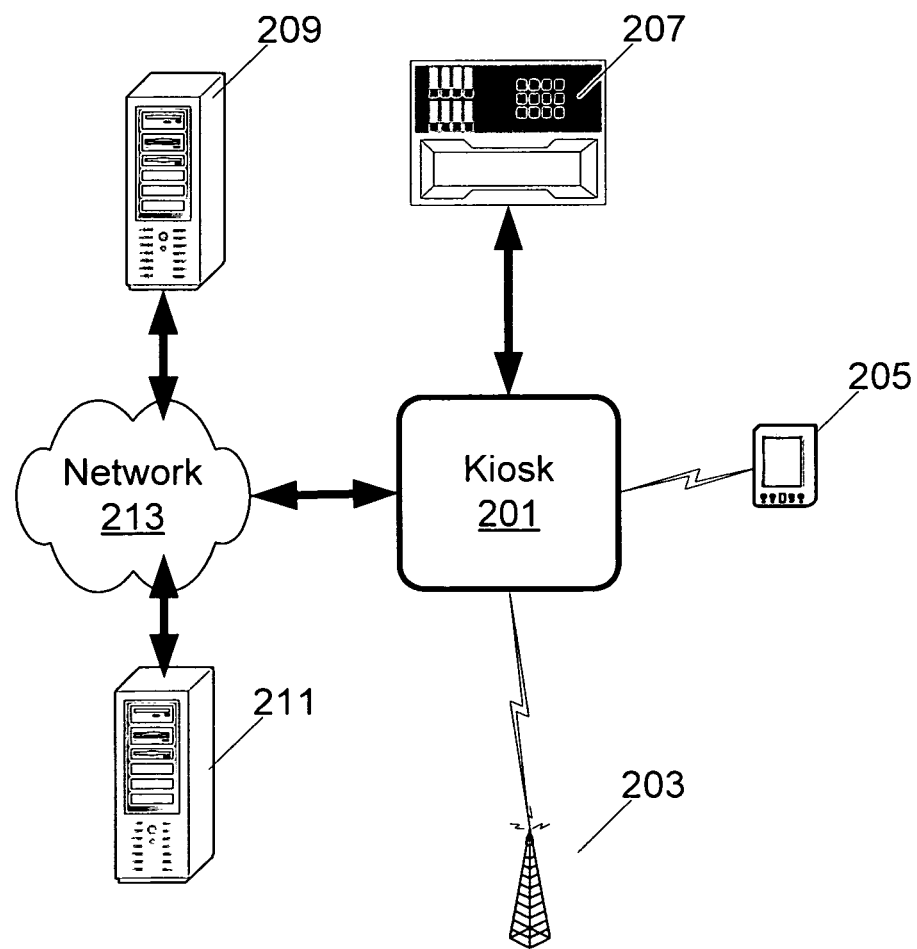
FIG. 2 is a schematic diagram of the network operating environment 300 of the kiosk within an embodiment of the invention.

FIG. 2 is a schematic diagram of the network operating environment 200 of the kiosk within an embodiment of the invention. As illustrated, the kiosk 201 is communicably linked to a phone system 307, such as via ordinary phone lines. The kiosk 201 is also linked wirelessly to a cellular network 203 and a local wireless device 205, e.g., a Bluetooth equipped device. The local wireless link allows the user to use their own phone to communicate to or from the kiosk as well as to place a call through the kiosk to a customer service representative or advisor.

Finally, the kiosk 201 is linked via a network 213 to a number of networked data sources/sinks, e.g., servers 209, 211. In an embodiment of the invention, server 209 is an operator server of the company or other entity responsible for the kiosk. For example, LifeClinic® is the operator of kiosks that are placed in thousands of locations across the country. In this embodiment of the invention, the other server 211 is associated with a sponsor or other entity interested in receiving data from the kiosks as will be discussed in greater detail below.

The data transferred over the network links to/from one or both of servers 209, 211 to/from the kiosk 100 includes in an embodiment of the invention any or all of the communication indicated herein, including but not requiring: waiver, identity, readings, demographics and other data from the kiosk 100; instructions, video, communications, prior readings, and advertisements from the server(s) 209, 211.

Figure 3:
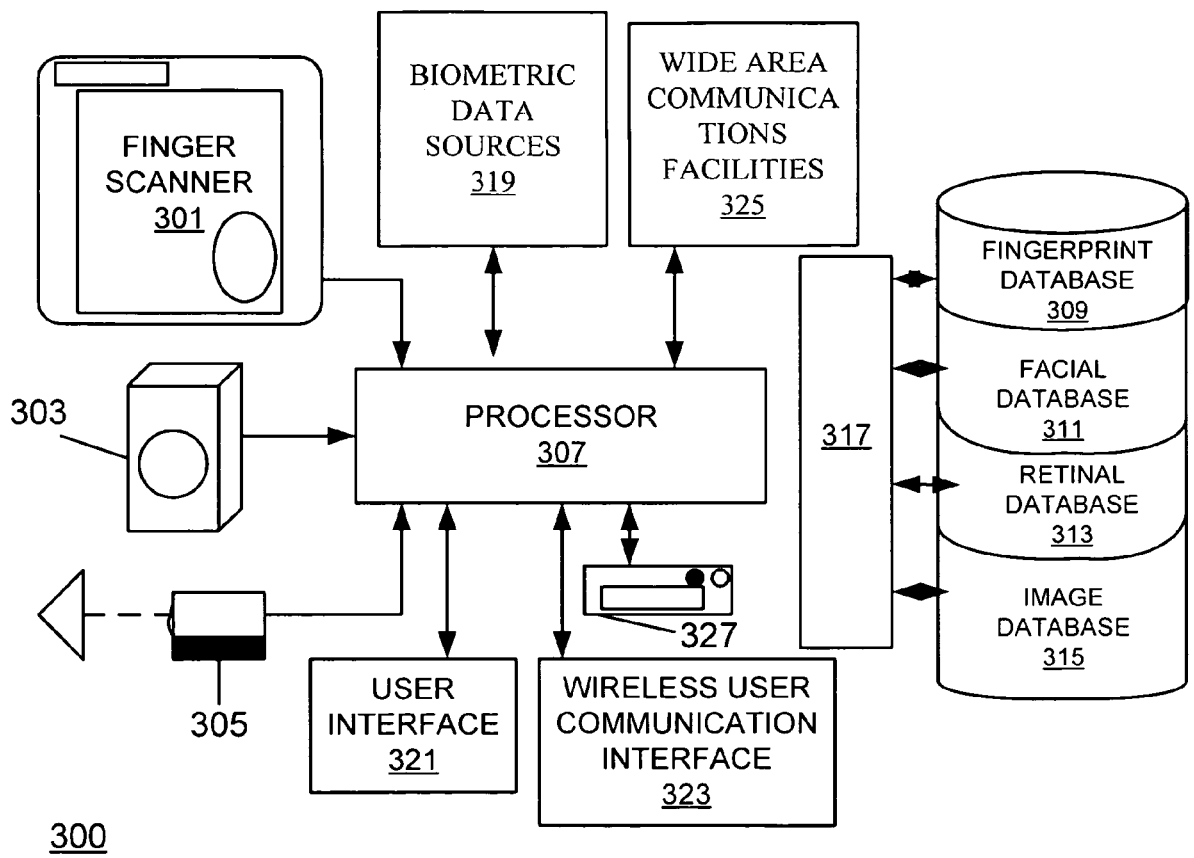
FIG. 3 is a schematic diagram of a security-enhanced biometric kiosk unit according to an embodiment of the invention.

FIG. 3 is a more detailed schematic diagram of a security-enhanced biometric kiosk unit according to an embodiment of the invention, showing the components and logical units of the system rather than the physical interconnections. Although the illustrated exemplary kiosk architecture includes features for both user verification and user security, it will be appreciated that aspects of the invention may be implemented using either or both sets of features.

The security-enhanced biometric kiosk 300 comprises at its core a processor 307 linked to various other system components. The processor may be of any suitable type including one or more microprocessors, programmable logic controllers, and so, and may be implemented within a personal computer, workstation, or other computing device, or may be integrated into the kiosk 100 in a customized form. Although the processor 307 is illustrated as being directly linked to individual components, it will be appreciated that the illustrated interconnections are exemplary. Components may be interconnected via other components and may also be interconnected by a common bus architecture.

As illustrated in FIG. 3, the processor 307 is linked to a set of verification input devices including, in the illustrate arrangement, a fingerprint scanner 301, a camera 303, and a retinal scanner 305. It will be appreciated that other types of verification devices may be used instead or in addition to those listed. Moreover, although the camera 303 and retinal scanner 305 are illustrated as separate components, they may share one or more components, e.g., optics, etc. As will be appreciated, commercial camera systems, both built in (e.g., in a lap top computer) and stand alone, exist that are capable of executing face tracking and face recognition tasks.

The fingerprint scanner 301, camera 303, and retinal scanner 305 are communicably linked to the processor 307. The processor 307 is similarly linked to a series of databases through a database interface 317. The illustrated databases include a fingerprint database 309, a facial feature database 311, a retinal feature database 313, and an image database 315. The processor 307 is also linked to other components of the kiosk including a user interface 321, such as a screen, speaker, keyboard, buttons, etc. Additional components include biometric data sources 319 for kiosks that measure such information. The biometric data gathered by sources 319 can include parameters such as user weight, blood pressure, pulse rate, body fat and blood oxygen, or other parameters as will be appreciated by those of skill in the art.

The processor 307 is further linked to a wireless communication interface 323. The wireless communication interface 323 provides a mechanism for wirelessly communicating with nearby electronic devices. For example, the wireless communication interface 323 is adapted in an embodiment of the invention to wirelessly call a user's, cell phone and connect the user via wide area communications facilities 325 to a call center or emergency personnel. As will be discussed in greater detail below, this functionality allows a user to be connected to necessary personnel in the event of an abnormal biometric reading, such as an extremely high blood pressure reading. In this way, the user is given counseling and advice to facilitate appropriate treatment or explain any complications. The user may also call a number, e.g., a 1-800 or other toll-free number, to initiate a consultation or get answers to general questions.

The processor 307 may also be linked to a card reader 327. A user may apply for and acquire a health information card, e.g., a co-branded magnetic stripe card promoted by the owner/operator and a credit card company or other enterprise. At the time that the user applies for the card, they preferably supply their name and address and may also be asked to respond to other questions that are of significance with respect to marketing. At that time as well, the customer may also be asked to sign a waiver at the information desk whereby they agree that their name and/or other information can be used for promotional and/or advertising purposes by the owner operator, etc. At the time that the user signs for and obtains the card, they may also have their personal security parameters gathered, e.g., face scan, retina scan, fingerprint, and so on. The user is then given a bar coded or magnetic coded loyalty card that encodes or is linked to his or her identification, address, etc. It will be appreciated that the user may instead sign up for the service on-line via the interface and connectivity of the kiosk itself, or from a personal computer or other networked computing device (e.g., personal digital assistant, Internet-enabled cell phone, etc.). In this case, the waiver may either be executed electronically or may be printed, executed, and mailed. The user card may be the user's credit card or other card carrying encoded user-specific identifying information.

When the user subsequently uses the kiosk, they are asked to scan their bar code by the bar code reader. This allows the kiosk to retrievably store the user's readings and also to access the user's name, address, etc. for promotional purposes. A waiver may appear on the display at this time as well. In addition, the data provided by a gift card or a credit card may also provide a buying history of the user to allow customization of messages and advertising. For example, the kiosk could recommend products similar to those that the user had purchased recently. Additionally, the kiosk may provide customized coupons based on the user's demographic data (race, class, income, age, ethnic origin, language, location, dwelling type, family size/type, gender, occupation, etc.) or buying history.

The fingerprint scanner 301 operates in a manner familiar to those of skill in the art, either alone or in conjunction with processes executed on processor 307 or other component. The fingerprint scanner 301 obtains an image of a user's finger compares this image to pre-scanned images, e.g., in database 309, to determine the identity of the user by determining whether the patterns of ridges and valleys in the images match. Although the fingerprint scanner 301 may be of any suitable construction, it will be appreciated that fingerprint scanners generally utilize either optical or capacitive technologies.

Optical scanners generally employ a charge coupled device (CCD) to capture the print image. Typically, an analog-to-digital converter in the scanner system processes the analog electrical output of the CCD to generate a digital image. The fingerprint scanner may comprise a light source such as an LED array to facilitate image acquisition. Much like optical scanners, capacitive fingerprint scanners also generate an image of a fingerprint. However, rather than using photons, they employ changes in capacitance across the print. One advantage of capacitance type sensors is that they cannot be manipulated via an image of a fingerprint. Additionally, capacitive scanners can be made more compact than optical devices.

As noted above, the camera 303 can be used for either or both of image storage, i.e., for later verification, and face recognition. For image storage purposes, the camera 303 is linked via the processor 307 to an image database 315. A photograph of each user is obtained by the camera 303 and stored, e.g., in database 315, for later verification if needed.

For purposes of facial recognition, the camera 303 captures an image of the users face and uses this image to verify the user's identity. Human faces have certain distinguishable features or landmarks. For example, there are distinct dips and rises that make up different facial features. Depending upon the algorithm used, as many, as 80 landmarks may be identified and used for recognition.

Examples of landmarks include the distance between a user's eyes, the width of a user's nose, depth of a user's eye sockets, shape or location of a user's cheekbones, shape or location of a user's jaw line, and the shape or location of a user's chin. Features of the landmark points are measured and translated to a unique numerical code or "faceprint" that represents the particular face. Pre-scanned faces, or related representations such as face prints, are stored in database 311 to facilitate later comparison for validation. Registration of a user's faceprint to be used for later verification may occur upon the user's first use of a kiosk system as described herein, or may be obtained elsewhere, e.g., at a registration desk.

The retinal scanner 305 obtains an image of the user's retina and compares this to prior scans, e.g. scans stored in database 313, to verify a user's identity. Retinal scanners are commercially available, and operate in a manner similar to that described above, i.e. by matching a retina of interest, or characteristics thereof, to a validation image of a retina or to characteristics of such an image.

It will be appreciated that other identity verification techniques may be used additionally or alternatively to verify a user's identity. Other techniques include, but are not limited to, voiceprint recognition, vein pattern recognition, iris recognition, etc.

While the databases 309, 311, 313, and 315 may be local to the kiosk, it is preferred that alternatively or additionally, there are databases that are accessible by the kiosk in question as well as other kiosks so that a user may access their information at any one of a global network of kiosks. Thus, the databases 309, 311, 313, and 315 are preferably stored or replicated at one or more central servers and may be downloaded periodically or as needed, or may be queried rather than downloaded.

The aforementioned security and verification features are important not only to prevent unauthorized access to a user's private data, but also to protect sponsors or affiliates from fraud. For example, it is important for kiosk sponsors and affiliates who provide incentives linked to user health to be able to verify that the user is indeed the person that they purport to be.

One area where significant incentives may be provided and hence where enhanced security will be important is the area of insurance incentives. In particular, insurers will enroll with a kiosk system host to receive user medical information from such kiosks and to provide targeted advertising and incentives through the kiosks. In particular, a user may use any one of the global network of kiosks to take a measurement of interest, e.g., weight, body fat percentage, or blood pressure, and this information will be transmitted to the enrolled insurer. In an embodiment of the invention, the kiosk displays a list of enrolled insurers to the user, and the user selects the appropriate company name.

If the user's current and prior measurements show a positive trend (e.g., losing body fat) at an acceptable rate (e.g., 2 pounds per week) or in an acceptable amount (e.g., 10 pounds), then the insurer will provide a reward to the user. Rewards can consist of rebates, gift cards, reduced insurance rates, and so on. Thus, users may be tempted to cheat to obtain the incentives, i.e., by having a friend in better health sit in as the user. To avoid fraud and cheating, it is important that the insurer be able to verify that the subscriber being rewarded has indeed made the appropriate improvements.

In an embodiment of the invention, the kiosk, whether providing health-related measurements or not, displays information of general interest to the user. For example, the kiosk may display a stock ticker or 5-day weather forecast.

Kiosks of the type described above can be used for a number of activities and interchanges that provide value to both the community and the sponsor or business supporting the machine. For example, the kiosk, whether or not it includes a biometric measurement facilities, can be used to provide entertainment such as via television or video. The entertainment content may be customized for the sponsor, e.g., a department store, or may be publicly available entertainment. In this embodiment of the invention, the entertainment provides a draw for customers who may not be interested in shopping or may be tired.

For examples, men accompanying women in a predominantly female-oriented store may prefer to rest at the kiosk. In an embodiment of the invention wherein the user identifies themselves by swiping a loyalty card, credit card, etc., the system can provide customized services. For example, if the system is able to access recent purchase history, it will supply appropriate coupons via the attached printer to encourage the user to avail themselves of the goods or services of the sponsor. More generally, a credit card or gift card's magnetic stripe may supply identity information both for customization of services and to track a user's biometric readings.

In this embodiment of the invention, the user may be presented with menu options to choose an activity. For example, a user may be asked to choose from sports scores, sports highlights, interviews, news, current affairs, exercise tips, etc. In another example of the invention, the kiosk provides one or more maps or informational items related to the store hosting the kiosk. Advertisements are run during these services and can be customized if the customer uses a personalized gift card or credit card.

Figure 4:
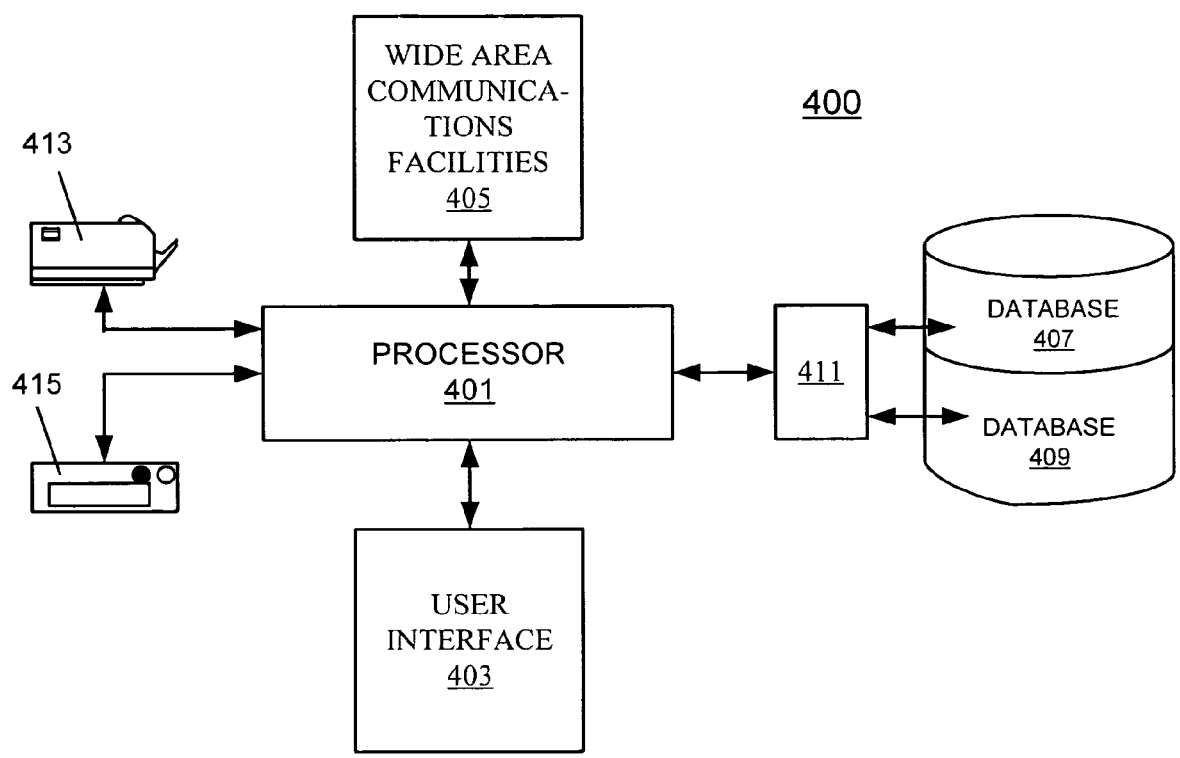
FIG. 4 is a schematic diagram of a non-biometric entertainment-enhanced kiosk unit according to an embodiment of the invention.
Figure 6:
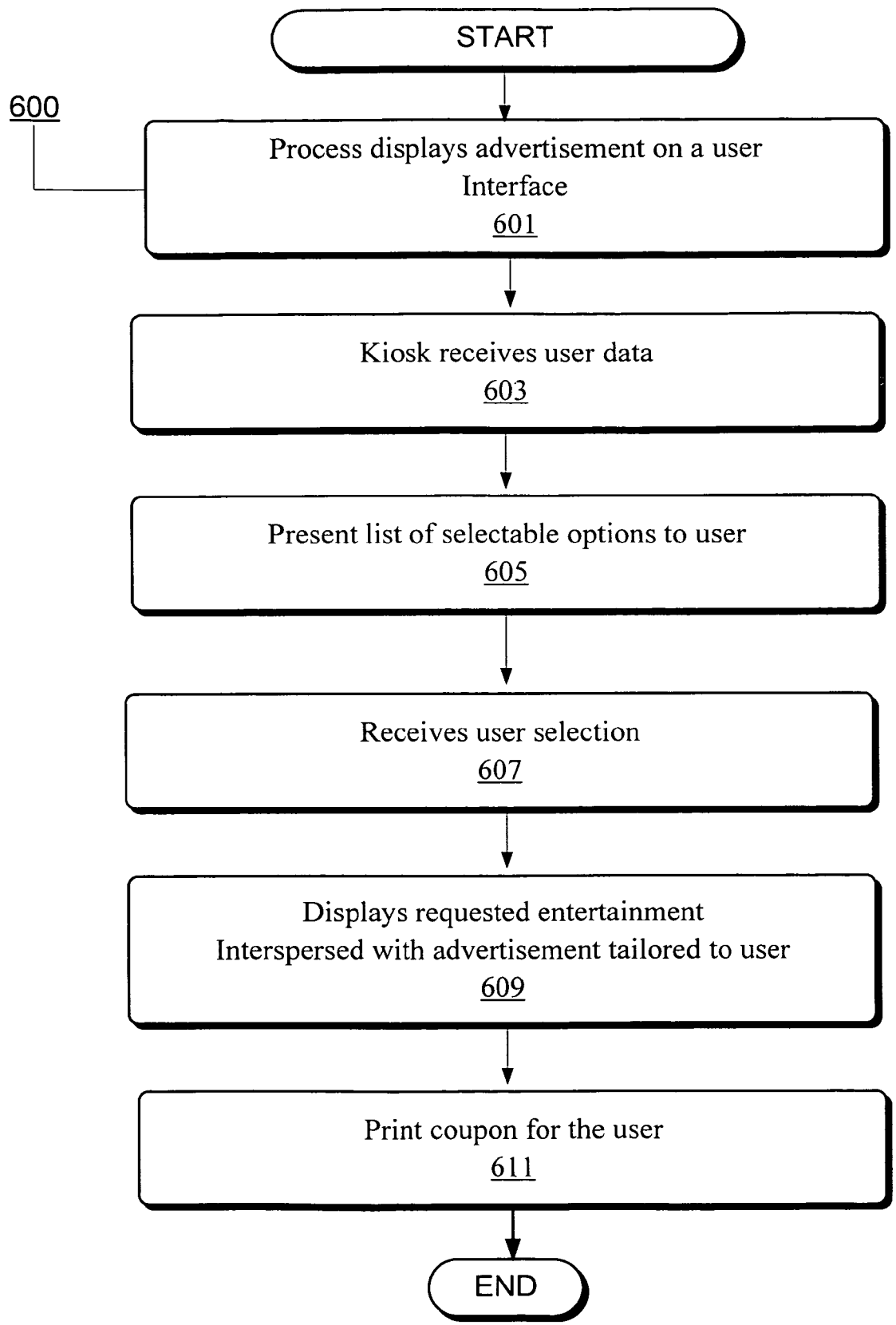
FIG. 6 is a flow chart showing a process of providing entertainment and advertising to users via a non-biometric kiosk according to an embodiment of the invention.

A schematic diagram of an exemplary kiosk that omits biometric measurement and information facilities but that provides entertainment information such as via television, video, etc., is illustrated in FIG. 4. The kiosk 400 is similar in some regards to that of FIG. 3, and includes a processor 401, a user interface 403, wide area communications facilities 405, and a set of databases 407, 409, linked to the processor 401 via a database interface 411. The kiosk 400 includes a printer 413, which may also be used in the kiosk 300 of FIG. 3. The kiosk 400 also includes a card reader 415. In overview, the non-biometric kiosk 400 as illustrated in FIG. 4 is usable to provide entertainment and advertising to users. The manner of operation according to a specific example will be given below by reference to the flow chart of FIG. 6.

Returning now to the system illustrated in FIG. 3, it was mentioned above that such a biometric measurement equipped kiosk can be used to obtain and provide biometric data of interest to a user and to provide an emergency alert to the user. In particular, certain biometric measurements can convey information sufficient to indicate whether the user may be in or about to enter a dangerous state. For example, blood pressure readings can indicate that a person is having, or is close to having, a stroke. In this case, the kiosk will call the user's cell phone automatically and connect the user to an emergency service, so that a paramedic may further diagnose and advise the user. This is especially useful for older users who may not be able to dial a help number. In particular, very high (or otherwise worrisome) readings cause the kiosk to connect the user's cell phone to the kiosk and then through to a call center representative for counseling. When communicating with the user's cell phone, the kiosk may target devices within a small enough radius to likely include the cell phone, e.g., 2 or 3 feet. The connection between the kiosk and the cell phone may be executed via Bluetooth or other suitable short-range wireless protocol.

Figure 5:
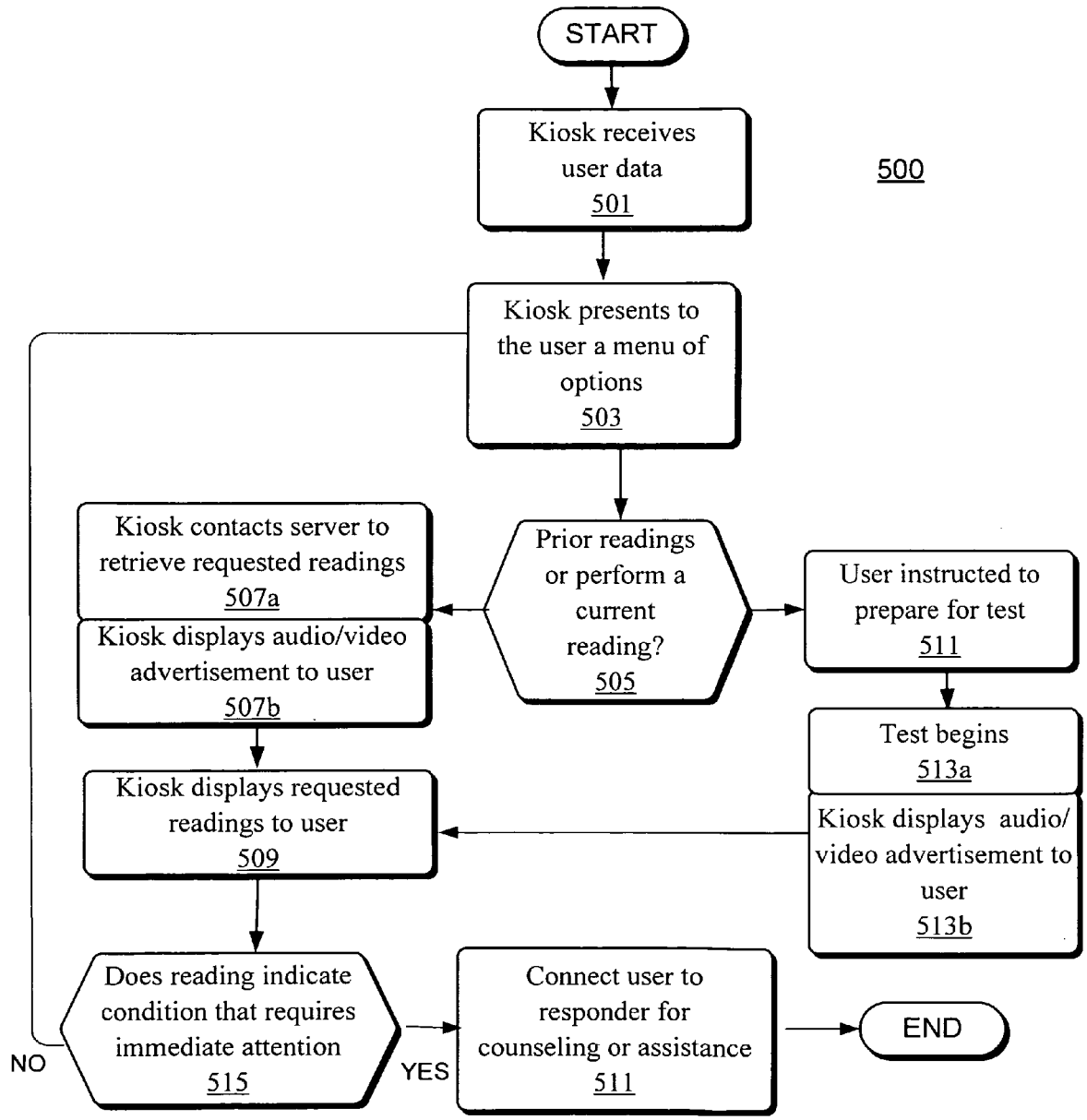
FIG. 5 is a flow chart showing a process of user alert and consultation for unusual reading conditions according to an embodiment of the invention.

A process of operation according to a specific example will be given below by reference to the flow chart of FIG. 5. At stage 501 of the process 500, the kiosk receives user data, such as pursuant to the swipe of a user magnetic stripe card in a card reader. At stage 503, the kiosk presents to the user a menu of options. In an embodiment of the invention, the options include an option to retrieve prior readings and an option to perform a current reading. If the user does not have a card or swipes a card for which no data is available, or if the user information associated with the card does not match the user identity derived from identity verification, e.g., via face recognition, the kiosk may so inform the user. For example, the visual user interface of the kiosk may display a message such as: "Customized services are not available due to lack of identity information/verification. Please visit [www.abc.com\the information desk\etc.] to [obtain a Heath Information Card\confirm identity\etc.]."

At stage 505, it is determined whether the user wishes to retrieve prior readings or perform a current reading. If the user desires to retrieve prior readings the process flows to stage 507a, whereat the kiosk contacts a server over a network or other link to retrieve the requested readings. During this time, at stage 507b, the kiosk may display an audio/video advertisement to the user. After the advertisement has played, the kiosk presents the requested readings to the user at stage 509 and returns to stage 503.

If at stage 505 it is determined that the user wishes to perform a current reading, the process flows to stage 511, whereat the user is instructed to prepare for the test, i.e., by placing their arm in the cuff, sitting appropriately on the scale/seat, gripping a handle in a specific location etc. At stage 513*a*, the test begins. Concurrently in stage 513*b*, the kiosk presents an audio/video advertisement to the user. After the advertisement has played, the kiosk presents the requested readings to the user at stage 509.

A stage 515, the kiosk determines whether the biometric reading given to the user in stage 509 indicates a physical condition that requires immediate attention. For example, as noted above, certain blood pressure readings or pulse rate readings may signal an ongoing or imminent serious physical problem such as a stroke. If it is determined at stage 515 that the biometric reading given to the user does not indicate a physical condition that requires immediate attention, then the process returns to stage 503. Otherwise, the process flows to stage 517, whereupon the kiosk connects the user to a responder, such as a call center representative or emergency personnel or doctor on call, and transmits data regarding the reading of concern to the responder. At this point, the responder is able to counsel the user or to summon the necessary aid.

As noted above, the non-biometric kiosk 400 as illustrated in FIG. 4 is usable to provide entertainment and advertising to users. The manner of operation according to a specific example is now shown by reference to the flow chart of FIG. 6. At stage. 601 of the process 600, the process displays advertisements on a user interface. Such advertisements may be still or video, and may be interspersed with directions for a user to swipe their card to access entertainment options. At stage 603, the kiosk receives user data, such as pursuant to the swipe of a user magnetic stripe card in a card reader. The data may either be stored on the card or the data stored on the card may be linked to the user data by the kiosk.

Upon receipt of the user data, the process flows to stage 605, whereupon a list of selectable options is presented to the user. Such options may include sports scores, sports highlights, interviews, news, current affairs, exercise tips, etc. At stage 607, the process receives a user selection of an option and at stage 609 proceeds to display the entertainment requested by the user. At the same time, the process may intersperse within the material advertisements customized to the user based on the user demographic or other data as gathered from the user's co-branded card.

Prior to ending, the process optionally prints a coupon for the user at stage 611. The coupon may be specific to a store within which the kiosk is hosted, or may be specific to a product sold in such store, or may simply be specific to the user demographics. Subsequent to stage 611, the process terminates.

Although the biometric service-providing kiosks discussed above may provide the measurement data as well as advertising and the other types of data discussed above, the kiosk also optionally provides customized user feedback in a further embodiment of the invention. For example, if the user has lost a certain amount of excess weight compared to a prior visit or visits, the kiosk will inform the user of the loss and will also provide a modified diet or exercise regimen to the user. The updated diet and/or regimen may be tailored to continue an appropriate weight loss, slow an excessive weight loss rate, or accelerate an inadequate weight loss rate.

In a further embodiment of the invention, the kiosk optionally modifies displayed advertising according to user health as indicated by the biometric measurements. For example, advertisements for snack foods are not appropriate for overweight users, whereas information on healthy eating programs and so on may be more appropriate.

As noted above, the kiosk may comprise an attached or integrated printing device. In this regard, the printer can be used to print out detailed customized instructions and programs for the user. For example, the updated diet and/or regimen may be printed out to be taken by the user. Preprinted materials may also be made available instead or in addition to the contemporaneously printed materials.

As discussed herein, video may comprise downloaded and/or streaming video, animation, etc, and may be accompanied by sound and/or other sensory information. All references cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for providing user data via a networked plurality of biometric measurement kiosks including one or more biometric measurement kiosks at each of a plurality of locations, the method comprising: facilitating a contest among a plurality of institutions via the networked plurality of biometric measurement kiosks including one or more biometric measurement kiosks at each institution, by: receiving, by each of the plurality of biometric measurement kiosks, user data from a respective user, the user data comprising user identity data; measuring, by each of the plurality of the biometric measurement kiosks, one or more fitness parameters of the respective user while in a state of rest including at least blood pressure; providing the measured data from each of the plurality of biometric measurement kiosks to a central device networked to the plurality of biometric measurement kiosks; and comparing the received measurements at the networked device to identify an institution having a highest level of fitness based on the measurements.

2. The method according to claim 1, wherein the one or more fitness parameters of the respective user include at least a body weight measurement.

3. The method according to claim 1, wherein the one or more fitness parameters of the respective user include at least one of a user body mass index measurement, and a user body weight measurement.

4. The method according to claim 1, further comprising conveying selected entertainment and advertisement information of one or more sponsors at the biometric measurement kiosk.

5. The method according to claim 4, wherein the selected entertainment and advertisement information includes four dimensional (4D) information for conveyance to four user senses.

6. The method according to claim 1, further comprising providing to the user a printed health recommendation including a suggested eating plan.

7. The method according to claim 6, wherein the printed health recommendation includes a product suggestion.

8. The method according to claim 4, further comprising one or more sponsor servers networked to the plurality of biometric measurement kiosks to provide sponsor information.

9. The method according to claim 1, wherein the user identity data includes information to positively identify the user.

10. The method according to claim 9, wherein the user identity data includes one or both of user visual appearance data and user iris data.

11. The method according to claim 1, further comprising presenting an option to the user to execute a waiver, allowing the name of the user to be used for promotional and advertising purposes.

12. The method according to claim 1, wherein receiving user data from a respective user includes collecting data from at least one of a student ID card and a co-branded bar code card.

13. The method according to claim 1, wherein the plurality of institutions via a networked plurality of biometric measurement kiosks belong to at least one of a university network, a secondary school network, a post-secondary school network, a hospital network, a government network, an airline club network, a traveler's network, a work site network, a health club network, food service and restaurant chains, financial institutions, convention centers, a doctor's office network and a hotel or hotel chains.

14. The method according to claim 1, further comprising providing to a user an emergency notification or warning when a potentially dangerous condition exists.

15. A nontransitory computer-readable medium having thereon computer executable instructions for facilitating a contest among a plurality of institutions via a networked plurality of biometric measurement kiosks including one or more biometric measurement kiosks at each institution, comprising instructions for: receiving, by each of the plurality of biometric measurement kiosks, user data from a respective user, the user data comprising user identity data; measuring, by each of the plurality of the biometric measurement kiosks, one or more fitness parameters of the respective user while in a state of rest, including at least a measurement of blood pressure; providing the measured data from each of the plurality of biometric measurement kiosks to a central device networked to the plurality of biometric measurement kiosks; and comparing the received measurements at the networked device to identify the institution having a highest level of fitness based on the measurements.

16. The nontransitory computer-readable medium according to claim 15, further comprising instructions for displaying selected entertainment and advertisement information of one or more sponsors at the biometric measurement kiosk.

17. The nontransitory computer-readable medium according to claim 15, further comprising instructions for presenting an option to the user to execute a waiver, allowing the name of the user to be used for promotional and advertising purposes.

18. The nontransitory computer-readable medium according to claim 15, wherein the instructions for receiving user data from a respective user include instructions for collecting data from at least one of a student ID card and a co-branded bar code card.

* * * * *